US00PP11786P2

(12) United States Plant Patent
Berres

(10) Patent No.: US PP11,786 P2
(45) Date of Patent: Feb. 20, 2001

(54) OSTEOSPERMUM PLANT NAMED 'ARCTUR'

(75) Inventor: Marcus Berres, Bingen (DE)

(73) Assignee: Innovaplant GmbH & Co. KG, Gensingen (DE)

( * ) Notice: Under 35 U.S.C. 154(b), the term of this patent shall be extended for 0 days.

(21) Appl. No.: 09/291,107

(22) Filed: Apr. 14, 1999

(51) Int. Cl.[7] ..... A01H 5/00
(52) U.S. Cl. ..... Plt./360
(58) Field of Search ..... Plt./360

(56) References Cited

PUBLICATIONS

UPOV CD–ROM, PBR 952509, Osteospermum designated Arctur, 1996.*

* cited by examiner

*Primary Examiner*—Bruce R. Campell
*Assistant Examiner*—Melissa L. Kimball
(74) *Attorney, Agent, or Firm*—C. A. Whealy

(57) ABSTRACT

A distinct cultivar of Osteospermum plant named 'Arctur', characterized by its compact, upright and somewhat outwardly spreading plant habit; freely branching, dense and bushy appearance; early and continuous flowering; elongated white ray florets with purple gray-colored lower surfaces and blue-tipped disc florets; and good summer performance.

1 Drawing Sheet

BACKGROUND OF THE INVENTION

The present invention relates to a new and distinct cultivar of Osteospermum plant, botanically known as *Osteospermum ecklonis* and referred to by the cultivar name Arctur.

The new cultivar is a product of a planned breeding program conducted by the Inventor in Gensingen, Germany. The objective of the breeding program was to create new Osteospermum cultivars with early flowering, good branching and improved summer performance.

The new cultivar originated from a cross made by the Inventor of the *Osteospermum ecklonis* cultivar Sunny Boy, not patented, as the female, or seed, parent and an unnamed proprietary selection of *Osteospermum ecklonis* as the male, or pollen, parent. The new Osteospermum was selected by the Inventor as a flowering plant within the progeny of this cross in a controlled environment in Gensingen, Germany, in the summer of 1994.

Plants of the new cultivar are different from plants of the female parent, the cultivar Sunny Boy, in the following characteristics:

1. Plants of the Osteospermum are more compact than plants of the cultivar Sunny Boy.

2. Plants of the new Osteospermum are more freely branching than plants of the cultivar Sunny Boy.

3. Plants of the new Osteospermum flower about two weeks earlier than plants of the cultivar Sunny Boy.

4. Plants of the new Osteospermum have more pointed ray florets than plants of the cultivar Sunny Boy.

5. Plants of the new Osteospermum have shorter peduncles than plants of the cultivar Sunny Boy.

Plants of the new cultivar are different from plants of the male parent, the unnamed proprietary selection of *Osteospermum ecklonis*, in the following characteristics:

1. Plants of the new Osteospermum are larger than plants of the unnamed proprietary selection of *Osteospermum ecklonis*.

2. Plants of the new Osteospermum have larger inflorescences than plants of the unnamed proprietary selection of *Osteospermum ecklonis*.

3. Lower surfaces of ray florets of the new Osteospermum are purple gray in color whereas lower surfaces of ray florets of the unnamed proprietary selection of *Osteospermum ecklonis* are not purple gray in color.

4. Plants of the new Osteospermum have shorter peduncles than plants of the unnamed proprietary selection of *Osteospermum ecklonis*.

Asexual propagation of the new cultivar by terminal cuttings and by tissue culture at Gensingen, Germany, has shown that the unique features of this new Osteospermum are stable and reproduced true to type in successive generations.

SUMMARY OF THE INVENTION

The following traits have been repeatedly observed and are determined to be the unique characteristics of 'Arctur'. These characteristics in combination distinguish 'Arctur' as a new and distinct cultivar:

1. Compact, upright and somewhat outwardly spreading plant habit.

2. Freely branching, dense and bushy appearance.

3. Early and continuous flowering.

4. Elongated white ray florets with purple gray-colored lower surfaces and blue-tipped disc florets.

5. Good summer performance, flowering continues through summer.

Plants of the new Osteospermum can be compared to plants of the *Osteospermum ecklonis* cultivar Sparkler, not patented. However, in side-by-side comparisons conducted in Gensingen, Germany, plants of the new cultivar differ from plants of the cultivar Sparkler, in the following characteristics:

1. Plants of the new Osteospermum are much more compact than plants of the cultivar Sparkler.

2. Plants of the new Osteospermum are more freely branching than plants of the cultivar Sparkler.

3. Plants of the new Osteospermum have smaller leaves than plants of the cultivar Sparkler.

4. Plants of the new Osteospermum have smaller inflorescences than plants of the cultivar Sparkler.

The cultivar Arctur has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical flowering plant of 'Arctur'.

The photograph at the bottom of the sheet is a close-up view of typical leaves, an inflorescence bud and lower and upper surfaces of typical inflorescences of 'Arctur'. Foliage and floret colors in the photographs may appear different from the actual colors due to light reflectance.

DETAILED BOTANICAL DESCRIPTION

The following observations, measurements and values describe plants of the new cultivar grown with three plants in a 25.5-cm container in Bonsall, Calif., under outdoor, full-sun conditions with day temperatures ranging from 18 to 35° C. and night temperatures ranging from 13 to 18° C. Plants were pinched (terminal apex removed) one time about two weeks after planting rooted cuttings. Plants used for this description were grown for about 8 to 12 weeks after planting rooted cuttings.

Color references are made to The Royal Horticultural Society Colour Chart except where general terms of ordinary dictionary significance are used.

Botanical classification: *Osteospermum ecklonis* cultivar Arctur.

Parentage:

*Female, or seed, parent.*—*Osteospermum ecklonis* cultivar Sunny Boy, not patented.

*Male, or pollen, parent.*—*Unnamed proprietary selection of Osteospermum ecklonis.*

Propagation:

*Type.*—By terminal cuttings.

*Time to initiate roots.*—Summer: About 20 days at 22° C. Winter: About 23 days at 20° C.

*Time to develop roots.*—Summer: About 25 days at 22° C. Winter: About 28 days at 20° C.

*Rooting habit.*—Fibrous and freely branching.

Plant description:

*Appearance.*—Perennial herbaceous container and garden plant. Broad inverted triangle. Initially upright then outwardly spreading growth habit. Freely branching with about 4 to 5 lateral branches. Full plants with dense foliage and erect flower stems.

*Vigor.*—Moderately vigorous.

*Plant height.*—About 30 cm.

*Plant spread.*—About 25 to 30 cm.

*Lateral branch description.*—Length: About 28 to 30 cm. Diameter: About 4 mm. Internode length: About 0.5 to 1 cm. Texture: Very sparse hairs. Color: 144B to 144C.

*Foliage description.*—Leaves alternate, single. Quantity of leaves: Numerous, about 32 per lateral branch. Length, fully expanded leaves, basal: About 5.5 to 6.5 cm. Width, fully expanded leaves, basal: About 1.8 cm. Shape: Elliptic. Apex: Broadly acute. Base: Attenuate. Margin: Nearly entire with minute irregular teeth. Aspect: Mostly flat. Texture: Coarse; very minute hairs on lower surface. Color: Young foliage, upper surface: 146B. Young foliage, lower surface: 146C. Fully expanded foliage, upper surface: 146A. Fully expanded foliage, lower surface: 146B. Attenuated leaf base: 146D. Venation, upper surface: 146A. Venation, lower surface: 146B.

Inflorescence description:

*Appearance.*—Daisy-type composite inflorescence form; actinomorphic. Disc and ray florets arranged acropetally on a capitulum. Inflorescences displayed above and beyond the foliage, with about two inflorescences per peduncle; peduncles arising from leaf axils. Typically about 14 opened and unopened inflorescences per plant. Inflorescences last about one week. Inflorescences persistent.

*Flowering response.*—Plants flower continuously from April to October in the Northern Hemisphere.

*Fragrance.*—Not detected.

*Inflorescence size.*—Diameter: About 4.5 to 5 cm. Depth (height): About 1 cm. Diameter of disc: About 0.8 to 1 cm.

*Inflorescence buds.*—Length: About 1.4 cm. Width: About 8 mm. Shape: Ovoid. Color: 145B.

*Ray florets.*—Length: About 2.5 cm. Width: About 5 mm. Shape: Ligulate. Apex: Tri-dentate, minute. Base: Acute. Margin: Entire. Aspect: Flat. Texture: Smooth, satiny. Number of ray florets per inflorescence: About 14 in a single whorl. Color: When opening, upper surface: White, 155D. When opening, lower surface: 148B to 148C with darker central longitudinal stripe. Fully opened, upper surface: White, 155D, with light purple, 92B, at base. Fully opened, lower surface: 156A with four or five longitudinal narrow stripes close to 93B; apex, 157A.

*Disc florets.*—Shape: Tubular; slightly salverform; five-lobed, fluted at apex. Number of disc florets per inflorescence: Numerous, about 48. Length: About 4 mm. Width: About 2 mm. Color: Immature: 149D; apex, 98B. Mature: 149D; apex, 98B to 98C.

*Phyllaries.*—Shape: Linear. Apex: Narrowly acute. Margin: Entire. Quantity and arrangement: About 14 per inflorescence; whorled. Texture: Coarse. Color: Upper surface: 144B. Lower surface: 148B.

*Peduncle.*—Length: About 8 cm. Aspect: Moderately strong; inflorescences held above and beyond foliage. Texture: Hispid; granular. Color: 146C.

*Reproductive organs.*—Androecium: Present on disc florets only. Stamens: Five; fused. Anther shape: Oblong. Anther size: About 1.5 mm. Anther color:

21A. Pollen amount: Scarce. Pollen color: 21A. Gynoecium: Present on ray and disc florets. Pistils: One. Pistil length: About 5 mm. Stigma shape: Bipartate. Stigma color: 99B. Style length: About 3 mm. Style color: 145B. Ovary color: 145A.

*Seed, immature.*—Color: Green.

Disease resistance: Resistance to pathogens common to Osteospermum has not been observed on plants of the new Osteospermum.

Heat tolerance: Plants of the new Osteospermum have demonstrated good tolerance to high temperatures and exhibit good summer performance.

It is claimed:

1. A new and distinct cultivar of Osteospermum plant named 'Arctur', as illustrated and described.

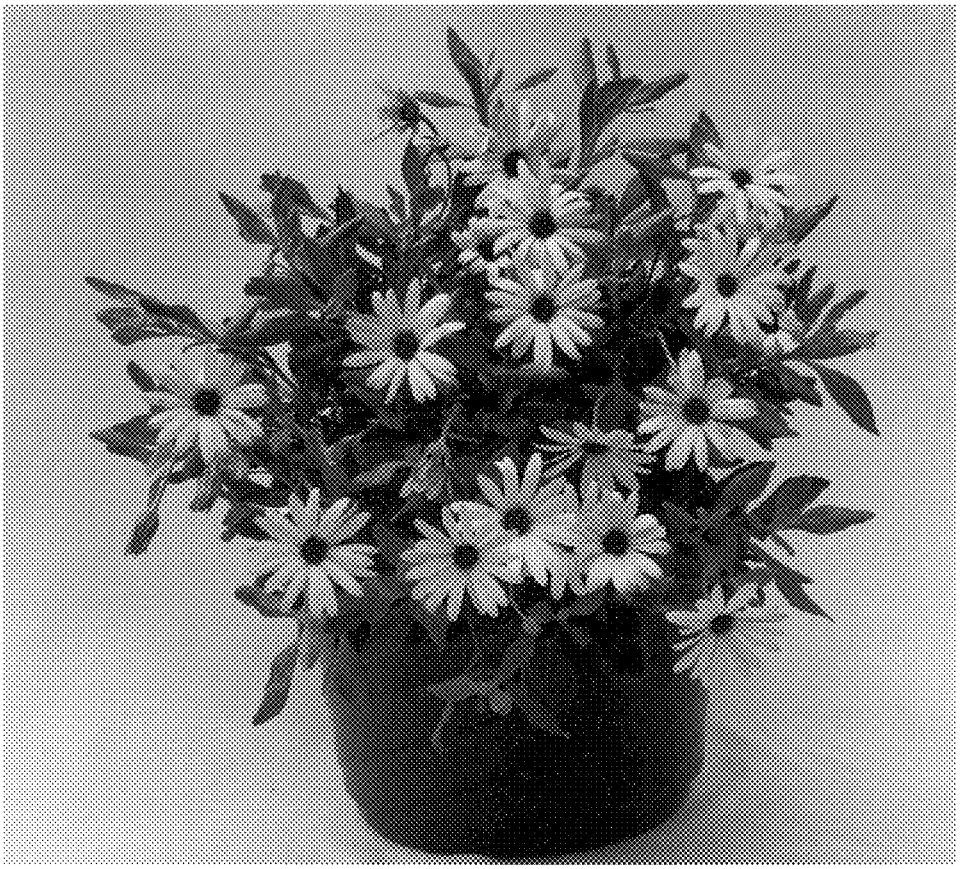
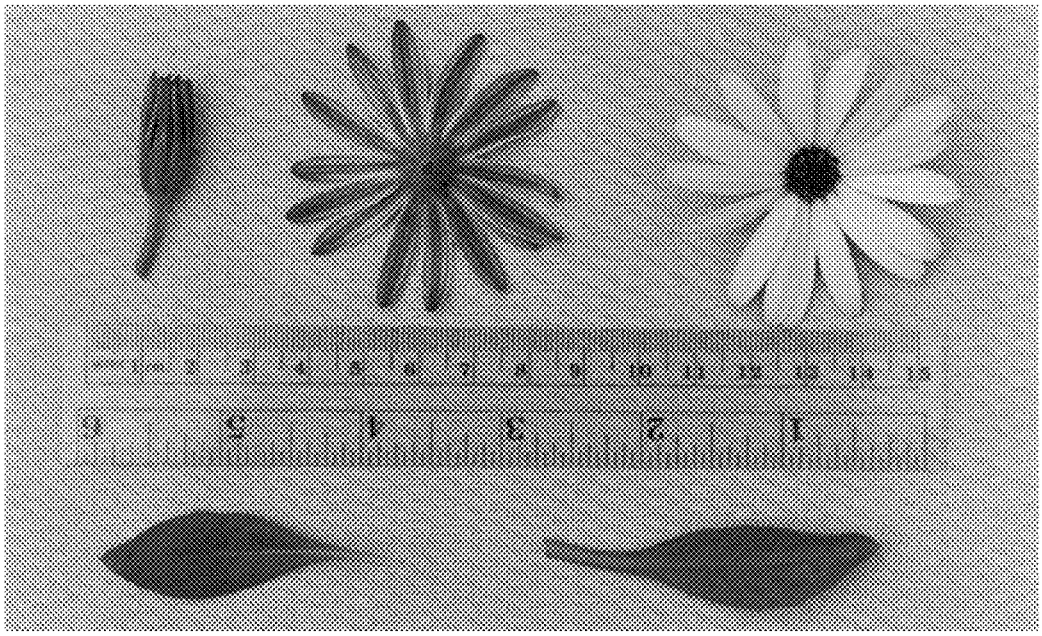

* * * * *